US009465011B2

(12) United States Patent
Vinogradov et al.

(10) Patent No.: US 9,465,011 B2
(45) Date of Patent: Oct. 11, 2016

(54) FLEXIBLE MAGNETOSTRICTIVE PROBE HAVING SENSOR ELEMENTS WITHOUT PERMANENT MAGNETS

(71) Applicant: Southwest Research Institute, San Antonio, TX (US)

(72) Inventors: Sergey A. Vinogradov, San Antonio, TX (US); Hegeon Kwun, San Antonio, TX (US); Darryl L. Wagar, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 451 days.

(21) Appl. No.: 13/864,696

(22) Filed: Apr. 17, 2013

(65) Prior Publication Data

US 2014/0312888 A1    Oct. 23, 2014

(51) Int. Cl.
*G01N 27/82* (2006.01)
*G01N 29/24* (2006.01)

(52) U.S. Cl.
CPC ..... *G01N 29/2412* (2013.01); *G01N 2291/106* (2013.01)

(58) Field of Classification Search
CPC ...... G01N 27/82; G01N 27/83; G01N 27/90; G01N 27/9013; G01N 27/9026; G01N 27/9033; G01N 27/904
See application file for complete search history.

(56) References Cited

U.S. PATENT DOCUMENTS

| 6,396,262 | B2 | 5/2002 | Light et al. |
| 6,917,196 | B2 | 7/2005 | Kwun et al. |
| 7,573,261 | B1* | 8/2009 | Vinogradov ............... 324/240 |
| 7,821,258 | B2 | 10/2010 | Vinogradov |
| 2004/0207528 | A1* | 10/2004 | Fabian et al. ............. 340/572.6 |
| 2010/0052670 | A1* | 3/2010 | Kwun et al. ................ 324/240 |
| 2010/0259252 | A1* | 10/2010 | Kim et al. .................. 324/240 |
| 2013/0069639 | A1* | 3/2013 | Cobb et al. ................. 324/209 |

* cited by examiner

*Primary Examiner* — Tung X Nguyen
*Assistant Examiner* — Feba Pothen
(74) *Attorney, Agent, or Firm* — Livingston Law Firm

(57) ABSTRACT

A sensor for use in magnetostrictive testing of a structure. An array of sensor elements is attached to a flexible backing. Each sensor element has a thin strip made from magnetostrictive material, a first coil wrapped around the width of the strip and operable to provide a DC bias magnetic field, and a second coil wrapped around the width of the strip and operable for MsS generation and detection. Typically, the first coils of all strips are electrically connected to each other and the second coils of all strips are electrically connected to each other, to form two separate coil circuits. The probe may be wrapped around the circumference of a cylindrical structure, and used for magnetostrictive testing.

16 Claims, 5 Drawing Sheets

FLEXIBLE MAGNETOSTRICTIVE PROBE HAVING SENSOR ELEMENTS WITHOUT PERMANENT MAGNETS

TECHNICAL FIELD OF THE INVENTION

This invention relates to nondestructive testing using guided wave and magnetostrictive sensor (MsS) technology, and more particularly, to an MsS probe used for magnetostrictive testing.

BACKGROUND OF THE INVENTION

Guided wave testing is widely used to inspect and monitor many types of structures. The method uses mechanical waves that propagate along a structure while guided by its boundaries. This allows the waves to travel a long distance with little loss in energy.

One type of guided wave testing is magnetostrictive sensor (MsS) testing, developed at Southwest Research Institute®. MsS testing was originally developed for guided wave wire rope and cable inspections, and earlier patents describing it are U.S. Pat. Nos. 5,456,113 and 5,457,994. A known MsS method generates (and detects) longitudinal guided waves directly in the cable. A known MsS probe for the method comprises an MsS wire coil and a DC biasing magnetic circuit. The MsS wire coil encircles the cable, and the DC biasing magnetic circuit is placed directly on the cable.

Various types of MsS probes may be used to implement MsS testing of wire ropes and cables. An MsS probe that is light-weight, relatively inexpensive, and operates independently of the cable material is described in U.S. Pat. No. 8,098,065.

MsS probes may be used to test structures other than cables, and the structure under test need not be cylindrical. Some MsS probes are designed for certain surface geometries, and some are adaptable for testing different surface geometries.

Various known MsS probes and MsS testing techniques, are described in the following patents, each incorporated herein by reference: U.S. Pat. No. 6,396,262 to Light, et al.; U.S. Pat. No. 6,917,196 to Kwun, et al.; U.S. Pat. No. 7,573,261 to Vinogradov; and U.S. Pat. No. 7,821,258 to Vinogradov.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION OF THE INVENTION

The wave modes used in MsS guided wave testing can be generally grouped into three types: the torsional, longitudinal and flexural modes. The MsS probe described herein is suitable for generating and detecting either longitudinal or flexural waves.

As described below, for testing cables, the MsS probe is attached around the circumference of the cable to generate longitudinal wave signals that propagate along the cable. The MsS equipment operates in a pulse-echo configuration, such that the probe is used for both the excitation and detection of the signals. At a location where there is a local structural anomaly in the cable, such as a change in its cross-section or stiffness, an echo is generated. Based on the arrival time of the echoes, and the predicted speed of the wave mode at a particular frequency, the distance of the feature in relation probe's location can be calculated.

In the examples of this description, the MsS probe and its methods are discussed in terms of non destructive testing (inspection and/or monitoring) of wire ropes, cables, anchor rods and similar longitudinal cylindrical structures (collectively referred to herein as "cables"). However, the probe described herein and the methods of using it are not limited to cables, and can be used to test any structure. The structure can be solid or "tubular", the latter meaning any long hollow structure, with cross sectional geometry that can be circular, rectangular or other, and can be closed or open channeled. The probe can be used in a flat configuration or shaped to fit a curved or other non planar surface under test.

The MsS probe described herein requires no permanent magnets, and is therefore lightweight and easy to install and use. It is operable independently of the cable material. Instead of using heavy magnets to generate the wave directly into the cable material, the wave is generated in a ferromagnetic strip and the vibrations transfer to the cable. It is easier to generate vibrations in the ferromagnetic strip because it has high permeability and magnetostriction coefficient.

Also, the MsS probe is flexible and could be described as a "flexible plate" probe. It may be used in a flat configuration or shaped around a cylindrical or other non flat surface. It can be easily wrapped around the circumference of a small diameter structure, such as a wire rope or cable. Thus, the MsS probe is especially suitable for testing wire cables, which are widely used in various structures as important load carrying members.

Figure 1:
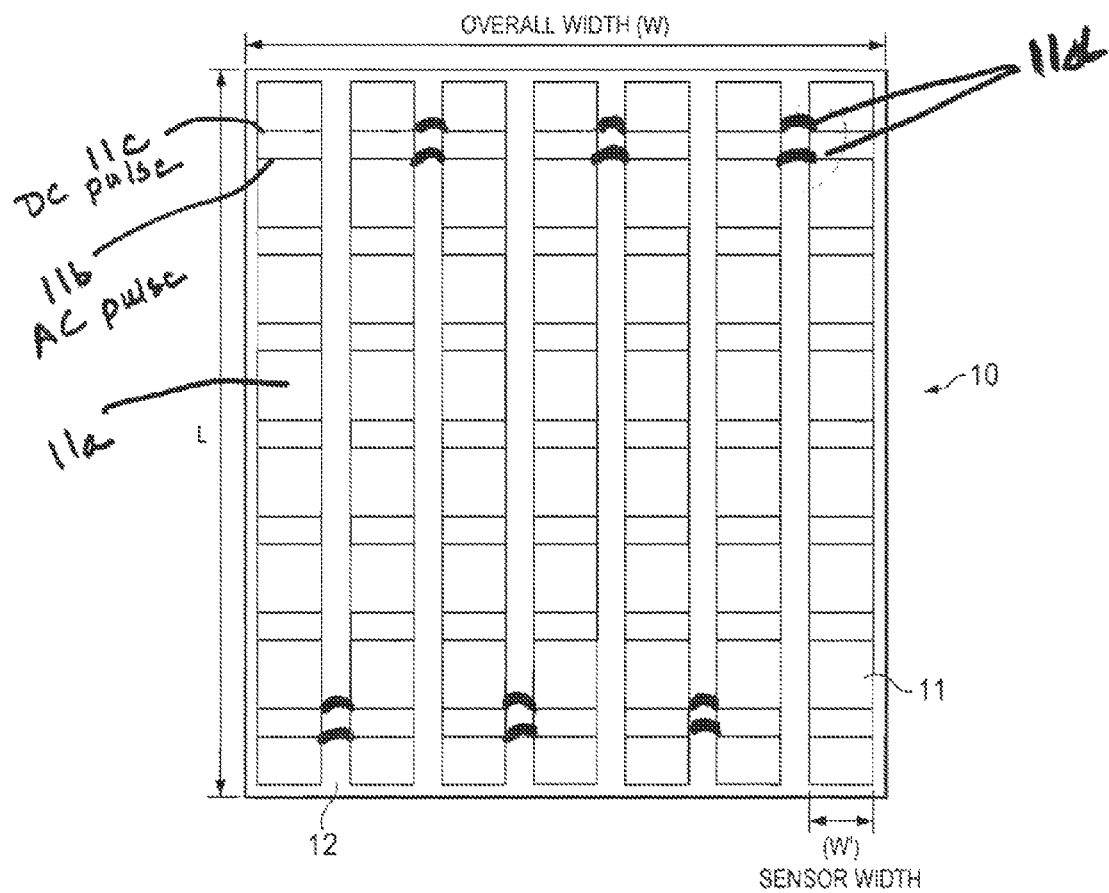
FIG. 1 is a schematic top plan view of an MsS probe for MsS testing.

FIG. 1 is a top plan view of an MsS probe 10 for MsS testing. The entire assembly of probe 10 is referred to herein as a "probe" as distinguished from the array of "sensor elements" 11 that it comprises.

A number of uniformly sized and shaped sensor elements 11 are arranged, side by side and parallel to each other, on a flexible backing material 12. In the example of FIG. 1, probe 10 has seven sensor elements 11. If probe 10 is to be used for testing cables, the overall width (W) of the probe 10 is made to be a little shorter than the overall circumference of a given cable.

Because sensor elements 11 are attached to a flexible backing 12, probe 10 may be fabricated as one continuous and flexible sensor array that can be curved and wrapped around a cable or other curved surface. Typically, backing 12 is sufficiently flexible so that if the structure being tested is cylindrical, such as a cable, probe 10 can be manually wrapped around and pressed against the structure.

In one embodiment, the dimensions of backing 12 and thus the overall dimensions of probe 10, are dictated by the circumference of the cable, so that the probe can be wrapped around the cable with only a slight gap between its edges. Backing 12 need only be slightly longer than the length of each sensor element 11 and slightly wider than the width of the array of sensor elements 11.

In other embodiments, probe 10 could be implemented as two separate, semi-circular shaped and semi-flexible arrays for easy mounting. In other words, probe 10 would be implemented in two parts, each to be wrapped around a semi-circular cross-section of the cable.

Examples of suitable materials for backing 12 are cork sheet, rubber, fiberglass or urethane. Backing 12 could also be a sheet of flexible metal of any type. An advantage of using a magnetic metal is that it would help to support the magnetic bias field oriented through the long axis of the sensor.

Although not explicitly illustrated, a layer of protective material may be applied to the contact surface of the sensor elements to protect the electromagnetic and MsS coils from damage during use. This protective layer protects the coil windings on the side of the sensor element facing the cable. The protective layer can be made from fiberglass soaked with epoxy, urethane, or certain metals. Preferably the protective layer is not a rubber material or other material that will inhibit transmission of vibrations to and from the ferromagnetic strip.

Figure 2:
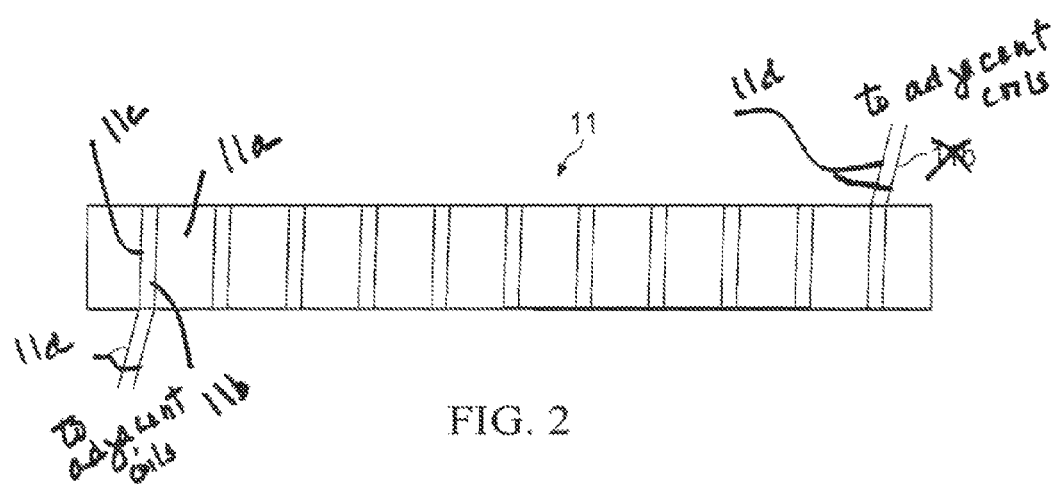
FIG. 2 is a top plan view of a single sensor element of the probe of FIG. 1.

FIG. 2 is a top plan view of a single sensor element 11 of probe 10. Referring to both FIGS. 1 and 2, each sensor element 11 comprises a thin strip 11a of magnetostrictive material and two separate coils 11b and 11c. In other words, each strip 11a is wound with two coils 11b and 11c. Each coil 11b and 11c is wound around the width (short axis) of the strip 11a.

By "magnetostrictive material" is meant a material that is capable of generating magnetostrictive vibrations. An example of a suitable material for strips 11a is a ferromagnetic alloy, such as FeCo.

The width of each magnetostrictive strip 11a and the total number of sensor elements 11 are chosen appropriately depending on the cable size, ease of fabrication, flexibility requirements, and requirements for mounting on and coupling to the cable under test. A typical width of each strip 11 is in the order of 0.1 mm. A probe 10 will typically have an array of at least four sensor elements 11.

For testing long cylindrical structures, such as cables, probe 10 is wrapped around the structure with the long axis (length, L) of sensors 11 aligned with the length of the structure. Because sensor elements 11 are thin in width, and because probe 10 has a number of sensor elements 11, strips 11a need not be made from a flexible material. As stated above, it is backing 12 that holds the sensor elements 11 together and allows probe 10 to be flexible.

The length of the magnetostrictive strips 11a is chosen appropriately depending on the desired center operating frequency of the MsS probe 10. For example, for a 20 KHz operating frequency, the length of each strip 11a would be approximately 50 mm.

One of the coils 11b is the "MsS coil", and is used for application of AC magnetic fields, and to generate and detect longitudinal guided waves in the strip 11a. The other coil 11c is the "electromagnetic coil", and is used to provide DC bias magnetic fields required for MsS operation. Notably, probe 10 does not require any permanent magnets because the DC biasing is achieved using coil 11c.

The magnetic fields from coils 11b and 11c are both located in the plane of strip 11a to produce longitudinal waves in the strip. In a cable, longitudinal waves are generated when a variable magnetic field is parallel to a permanent bias magnetic field and they are both parallel to the direction of the guided wave.

As illustrated by the connecting leads 11d in FIGS. 1 and 2, in typical applications, all sensor elements 11 of probe 10 have their respective coils connected. That is, all DC bias coils 11c are connected to each other, and all MsS coils 11b are connected to each other. As a result, probe 10 has two separate coil circuits, one for DC biasing and one for MsS generation and detection. The sensor elements 11 are then operated simultaneously to generate and detect longitudinal waves for inspection of the entire cross-section of a cable. However, as explained below in connection with FIGS. 6 and 7, because each sensor element 11 has its own strip 11a and its own coils 11b and 11c, each sensor element 11 is capable of being uncoupled from the others and operating independently as an MsS sensor. Or, the array of sensors can have their coils segmented into groups, such that sensor elements 11 are operated in groups.

Figure 3:
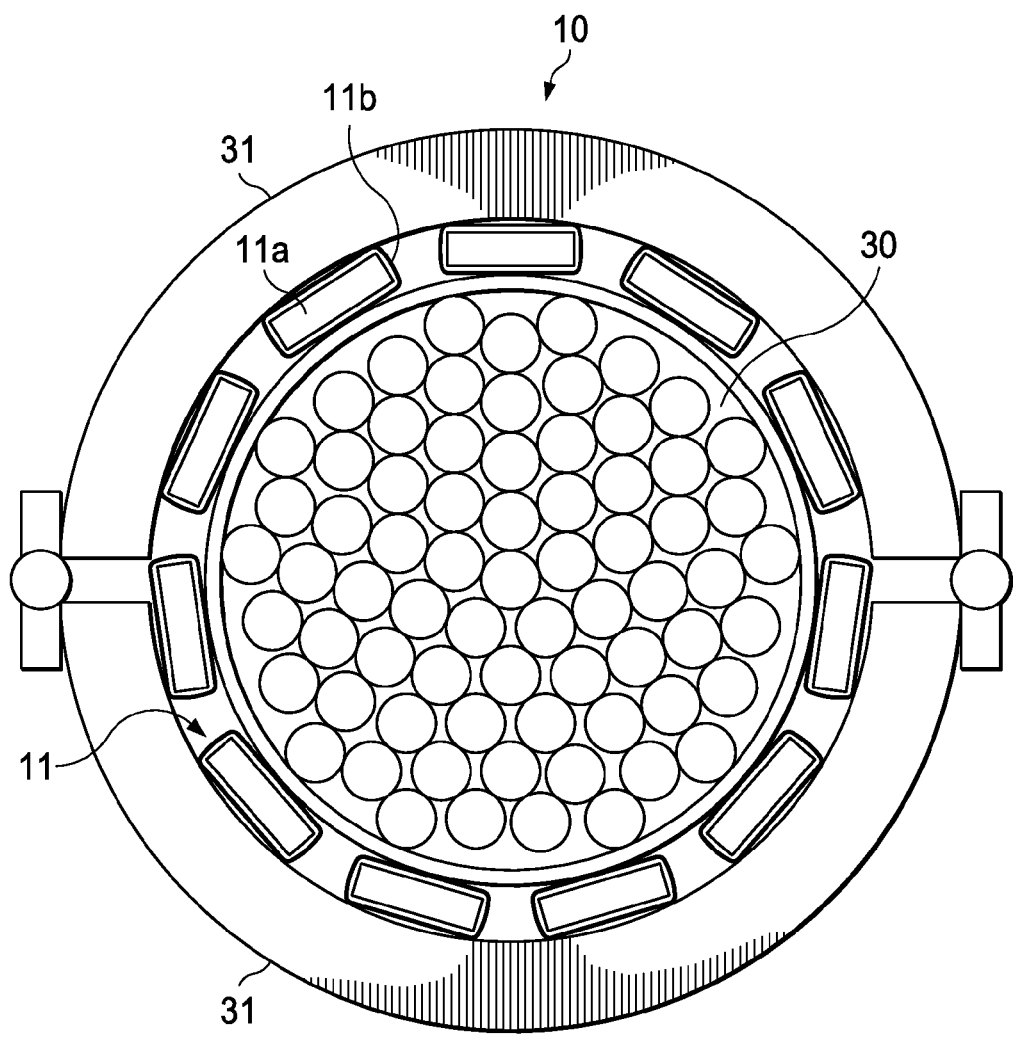
FIG. 3 is a cross-sectional view of the probe installed on a cable.

FIG. 3 is a cross sectional view of probe 10 installed on a cable 30. In this example, probe 10 has eleven sensor elements 11, which are shown in cross section across their widths (short axis). The long axis of each sensor element 11 is along the length of the cable.

A cross section of one coil 11b is represented, mainly to show how it is wrapped around the short axis of its associated strip 11a. However, for simplicity, the remainder of coils 11b and 11c are not explicitly illustrated. A feature of probe 10 is that it does not use a coil that encircles the cable.

Probe 10 may be wrapped around and compressed against the cable 30 with a clamping device 31. In addition, to maintain the mechanical coupling of guided waves between the probe 10 and cable 30, the probe could be adhesively bonded to the cable.

In general, coupling may be achieved in various ways, such as by manually or mechanically pressing the probe against the structure and/or by using a thin layer of adhesive between the bottom side of flexible backing 12 and the cable. The mechanical pressure may be supplied by using a clamp or bladder. As specific examples, coupling may be achieved by bonding the strip with adhesive material (such as epoxy), or by using a viscous coupling medium (such as shear wave couplant or honey), or by mechanically pressing the strip against the pipe with a mechanical tool (such as bladder or clamp), or by a combination of both mechanical and adhesive coupling.

Figure 4:
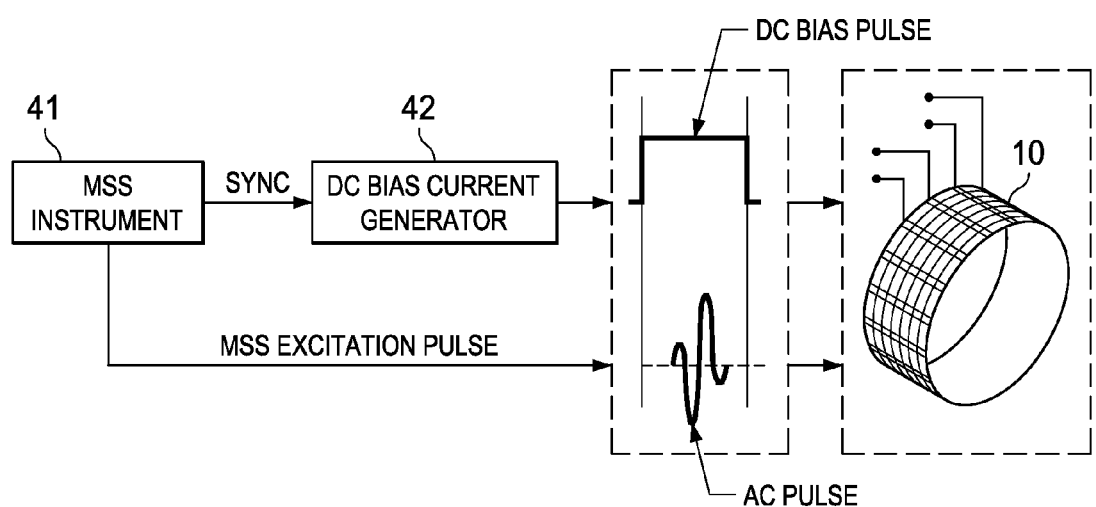
FIG. 4 is a block diagram of electronic instrumentation for implementing MsS testing with the probe.

FIG. 4 is a block diagram of electronic instrumentation for implementing MsS testing (immediate inspection and/or long term monitoring) with probe 10. Coil 11b has electrical leads for connection to an AC pulse. Coil 11c has electrical leads for connection to a DC bias pulse.

For operation, the MsS coil 11b is connected to MsS unit 41, which supplies a pulse of AC electric current to the MsS coil for guided wave generation. MsS unit 41 also detects the voltage signals induced in the MsS coil 11b by guided waves reflected back from irregularities. MsS unit 41 may be programmable to condition the detected signals in the MsS coil 11b, to acquire and display the detected signals and to save the acquired data. The electromagnetic coil 11c is connected to a power supply 42 that applies a DC electric current pulse to the coil to provide the DC bias magnetic fields needed for MsS operation.

In use, the probe 10 is placed around a cable under test, with the bottom surface of backing 12 against the outer surface of the cable. The probe 10 is then coupled to the cable as described above.

DC bias fields are established by applying DC current to coils 11b (typically connected together as a single coil) and inducing residual magnetization in ferromagnetic strips 11a. AC magnetic fields are applied in the lengthwise direction of the cable by applying an AC voltage to coils 11c (also typically connected together).

The guided waves generated in the magnetostrictive strips 11a of probe 10 couple to the cable and propagate along its length. When reflected waves from irregularities (herein referred to as "anomalies") in the pipeline (such as corrosion defects, notches, cuts, cracks or welds) return back to the location of probe 10, the waves are coupled to strips 11a. This induces voltage signals in MsS coils 11c through inverse magnetostrictive effects and are detected by MsS instrument electronics (not shown). Any reflected signals that return to the probe 10 are detected in reverse order.

As stated above, probe 10 is especially useful for long cylindrical structures that are small in diameter. These structures can be solid or hollow. Thus, in addition to cable testing (inspection and monitoring), the probe 10 can also be used for inspection and monitoring of rods (for example, anchor rods for towers).

However, as stated above, the same concepts can be applied to testing various other structures. The structure can be a long cylindrical structure that is hollow rather than solid, such as a pipeline. The probe 10 could be laid flat against a plate structure. Also, because the magnetostrictive vibration is produced inside ferromagnetic strips 11a, it can be transferred to (and from) a structure of any material, provided that appropriate mechanical coupling between sensor 20 and the surface under test is achieved.

Figure 5:
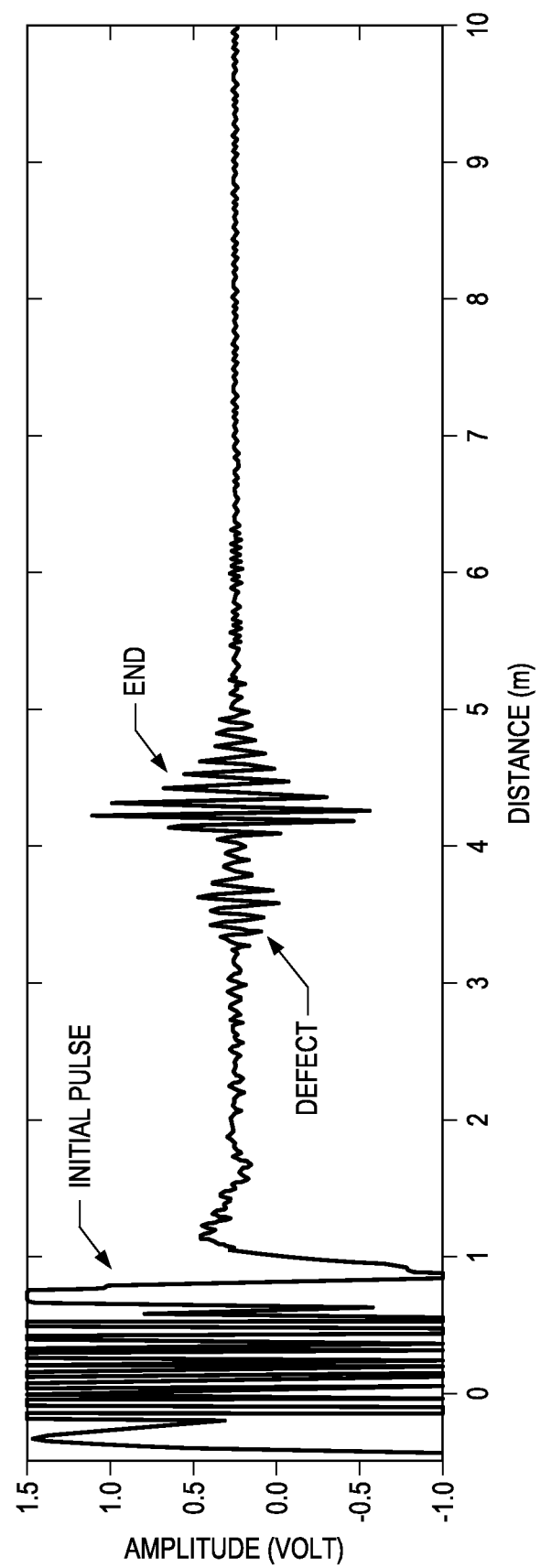
FIG. 5 illustrates longitudinal wave data obtained from a cable having a defect in one of its wires, using the probe.

FIG. 5 illustrates 30 kHz longitudinal wave data obtained from a cable having a defect in one of its wires, using probe 10. For this data, the cable was a 10 mm ground wire cable having a cut in one of its wire elements.

As stated above, in typical applications, all sensor elements 11 of probe 10 have their respective coils electrically connected for generation and detection of longitudinal waves. As a result, probe 10 has effectively a single DC bias coil made from the connected coils 11b, and a single MsS coil made from the connected coils 11c.

Figure 6:
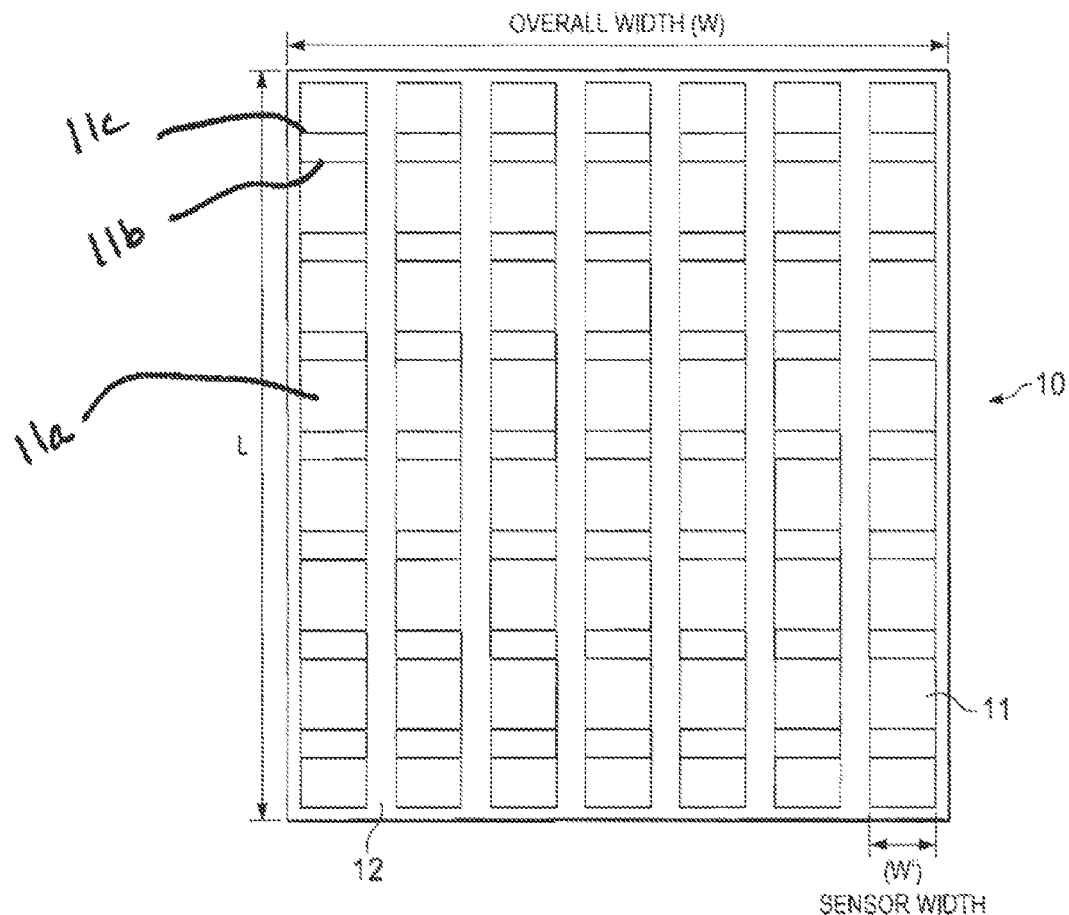
FIGS. 6 and 7 illustrate an alternative embodiment of the probe, with the sensor elements not being electrically connected to each other.
Figure 7:
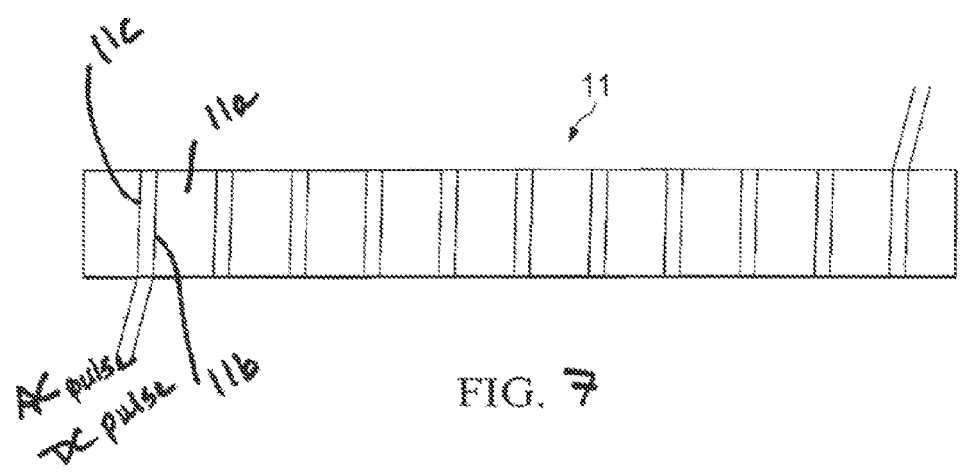

As illustrated in FIGS. 6 and 7, in an alternative embodiment of sensor 10, coils 11b and 11c may be segmented. In other words, instead of being electrically connected to form a single coil, coils 11b and 11c may be grouped into smaller groups of one or more coils each. These groups are electrically connected to form coil segments. The segments are groups of strips 11a and their corresponding coils 11b and 11c. In operation, the segmented coil pairs and their corresponding strips 11a may be activated and operated as individual MsS sensor groups for more detailed examination of a cable around its circumference.

Also, by operating individual sensor elements 11 (or groups of sensor elements) using multi-channel, MsS instrument electronics per a phased-array principle, probe 10 could be used to generate and detect flexural waves. Furthermore, by applying focusing techniques to sensor elements 11 with multi-channel electronics, probe 10 could also be used to examine a local area of the cross-section of large cables to produce a C-scan type image.

What is claimed is:

1. A probe for use in magnetostrictive sensor (MsS) testing of a structure, comprising:
    a flexible backing;
    a number of sensor elements attached to the backing, each sensor element being substantially larger in length than in width, the sensor elements being attached to the backing in a side by side pattern, parallel to each other;
    each sensor element comprising a thin strip made from magnetostrictive material, the strip having an elongated shape with a short dimension and a long dimension, a first coil wrapped around the short dimension of the strip and operable to provide a DC bias magnetic field, and a second coil wrapped around the short dimension of the strip and operable for MsS generation and detection;
    wherein the first coils of all strips are in parallel arrangement to the second coils of all strips; and
    wherein the first coils of all strips are electrically connected to each other and the second coils of all strips are electrically connected to each other, to form two separate coil circuits, such that a combination of DC current in the first coil and time-varying current in the second coil causes guided waves to be generated in the strips, which guided waves, when positioned against the structure, travel to and are reflected by anomalies in the structure.

2. The probe of claim 1, wherein the sensor elements are uniform in size and shape.

3. The probe of claim 1, wherein the backing is made from a non magnetic material.

4. The probe of claim 1, wherein the backing is made from a magnetic metal.

5. A probe for use in magnetostrictive sensor (MsS) testing of a structure, comprising:
    a flexible backing;
    a number of sensor elements attached to the backing, each sensor element being substantially larger in length than in width, the sensor elements being attached to the backing in a side by side pattern, parallel to each other;
    each sensor element comprising a thin strip made from magnetostrictive material, the strip having an elongated shape with a short dimension and a long dimension, a first coil wrapped around the short dimension of the strip and operable to provide a DC bias magnetic field, and a second coil wrapped around the short dimension of the strip and operable for MsS generation and detection;
    wherein the first coils of all strips are in parallel arrangement to the second coils of all strips;
    wherein the first coils of all strips are electrically connected in groups of one or more coils and the second coils of all strips are electrically connected in groups of one or more coils of corresponding strips, to form separate coil circuits, such that a combination of DC current in a group of the first coils and time-varying current in a corresponding group of the second coils cause guided waves to be generated in the corresponding strips, which guided waves, when positioned against the structure, travel to and are reflected by anomalies in the structure.

6. The probe of claim 5, wherein the sensor elements are uniform in size and shape.

7. The probe of claim 5, wherein the backing is made from a non magnetic material.

8. The probe of claim 5, wherein the backing is made from a magnetic metal.

9. A method using a magnetostrictive sensor for testing of a long cylindrical structure, comprising:
    placing a magnetostrictive probe against the surface of the structure, the probe having a flexible backing and a number of sensor elements attached to the backing, each sensor element being substantially larger in length than in width, the sensor elements being attached to the backing in a side by side pattern, parallel to each other;

each sensor element comprising a thin strip made from ferromagnetic material, the strip having an elongated shape with a short dimension and a long dimension, a first coil wrapped around the short dimension of the strip and operable as a DC biasing coil, and a second coil wrapped around the short dimension of the strip and operable to receive an AC current to operate as a magnetostrictive sensor coil;

wherein the first coils of all strips are in parallel arrangement to the second coils of all strips;

wherein the placing step is performed such that the lengths of the sensor elements are aligned with the length of the structure;

connecting one or more of the first coils to a DC biasing source;

connecting the corresponding one or more of the second coils to an AC source;

such that a combination of DC current in the connected first coils and time-varying current in the connected second coils cause guided waves to be generated in the strips, which guided waves, when positioned against the structure, travel to and are reflected by anomalies in the structure.

10. The method of claim 9, wherein the length of the magnetostrictive strips is chosen based on a desired center operating frequency of the probe.

11. The method of claim 9, wherein the guided waves are longitudinal waves.

12. The method of claim 9, wherein the guided waves are flexural waves.

13. The method of claim 9, wherein the placing step is performed such that the probe encircles the circumference of the structure.

14. The method of claim 9, wherein the placing step is performed such that the probe encircles part of circumference, and wherein the method is repeated for at least one additional probe placed around the remainder of the circumference.

15. The method of claim 9, wherein all first coils are electrically connected and operated as a single group, and all second coils are connected together as a single group.

16. The method of claim 9, wherein the sensor elements are electrically connected and operated in groups, such that the first coils of each group are electrically connected and operated together, and the second coils of each group are electrically connected and operated together.

* * * * *